United States Patent [19]

Wandell et al.

[11] Patent Number: 5,569,223
[45] Date of Patent: Oct. 29, 1996

[54] APPARATUS AND METHOD FOR ENHANCING BLOOD FLOW TO OBTAIN A BLOOD SAMPLE

[75] Inventors: Michael Wandell, Mercer Island, Wash.; Richard A. Quattrocchi, Barrington; Allan Frank, Chicago, both of Ill.

[73] Assignee: Home Access Health Corporation, Rolling Meadows, Ill.

[21] Appl. No.: 581,313

[22] Filed: Dec. 29, 1995

Related U.S. Application Data

[62] Division of Ser. No. 466,609, Jun. 6, 1995.

[51] Int. Cl.$^6$ .............................. A61M 35/00; A61M 5/32
[52] U.S. Cl. .............................. 604/290; 604/180
[58] Field of Search ........................ 604/289, 290, 604/304–308, 178, 180, 181; 602/41

[56] References Cited

U.S. PATENT DOCUMENTS 3,741,197 6/1973 Sanz et al. ........................ 604/305
4,978,342 12/1990 Heimreid ........................ 604/180
5,380,337 1/1995 Romaine ........................ 604/131

*Primary Examiner*—John G. Weiss
*Assistant Examiner*—David J. Cho
*Attorney, Agent, or Firm*—Rudnick & Wolfe

[57] ABSTRACT

A strip of pliable or flexible material that is sized to circumferentially extend about a digit of a person from whom a blood sample is to be taken. The strip of pliable material has upper and lower generally parallel and planar surfaces. Also, the flexible film or strip defines a throughhole between opposite ends of the film. The lower or bottom surface of the strip has a skin contacting adhesive thereon allowing the film to be tautly applied about the person's digit, with the throughhole circumscribing an underlying surface skin area that is to be punctured to create blood flow. The taut application of the strip about the digit inhibits venus blood return thus enhancing blood flow from the puncture and thereby providing an adequate blood specimen even in person's that have a difficultly bleeding. A method of obtaining a blood specimen is also disclosed.

2 Claims, 1 Drawing Sheet

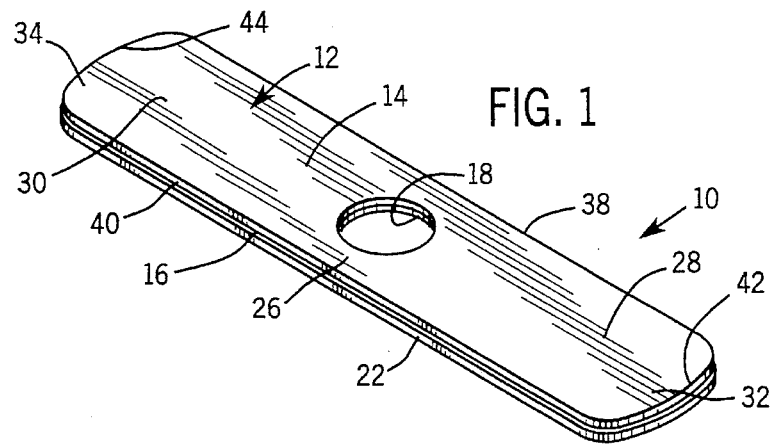
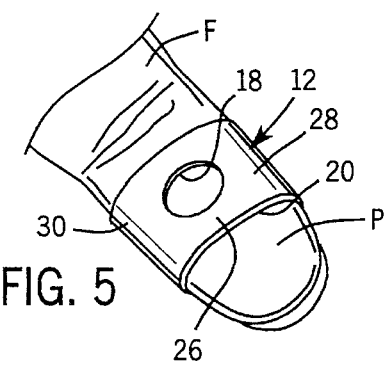
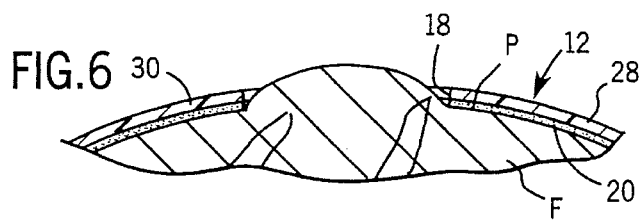

APPARATUS AND METHOD FOR ENHANCING BLOOD FLOW TO OBTAIN A BLOOD SAMPLE

This application is a division of patent application Ser. No. 08/466,609, filed Jun. 6, 1995, (pending).

FIELD OF THE INVENTION

The present invention relates to a method for obtaining a blood sample from a person's finger.

BACKGROUND OF THE INVENTION

Costs for the today's medical technology and practices have risen far faster than people's ordinary income. Accordingly, people are taking advantage of medical services at out-patient care facilities. Moreover, and when possible, many people are also starting to take advantage of in-home test kits to reduce theft medical costs.

Advantageously, medical technology has advanced wherein multiple human maladies and/or diseases are readily detectable from tests conducted of a blood specimen. Glucose and cholesterol levels may also be beneficially obtained from a blood sample. Because of today's medical advances, a small, substantially insignificant mount of blood i.e., a blood droplet, is usually adequate for today's blood testing techniques.

A professional at either a hospital or out-patient clinic will usually collect a blood specimen for analysis. The blood specimen is typically collected by puncturing a human digit, such as a finger or toe of the person being tested with a lancet or other suitable medical instrument to create a blood droplet or specimen. Home test kits are usually provided with a disposable lancet to create a puncture or prick in the person taking the test. Thus, collecting a blood specimen in connection with a home test kit is effected in generally the same manner as in a hospital or out-patient facility, except that either the person taking the test or another person uses the lancet or other medical instrument to create a blood droplet or specimen.

Besides the inherent problems of a person puncturing their own finger or having a non-professional attempt to collect a blood specimen, there are some instances where collecting a suitable blood specimen is complicated by other factors. Some people simply tend not to bleed. That is, some people have blood that tends to immediately coagulate, thus, making the collection of blood more difficult. Another common problem or complication in the blood collection process concerns the amount of blood collected. Understandably, people are reluctant to inflict pain onto themselves. Accordingly, the person taking the test at home may incorrectly use the lancet and, thus, will not obtain an adequate blood sample. Rather than reusing the lancet, people tend to smear the blood sample to make it appear adequate. Understandably, this problem is further complicated by those persons' whose blood clots quickly.

Unless an adequate blood specimen is obtained, the testing results may be affected. In the instance where the blood test was collected at a hospital or out-patient facility, either a second blood sample will be taken, or, if the person has left the facility, that person will have to return for another blood test. In home test kits, the failure to obtain an adequate blood specimen also can affect the results. If The test specimen is inadequate, the person may be required to purchase another kit to obtain another blood sample. In either event, costs to the person seeking the test results are increased. Moreover, valuable time is lost in the interim period, while exacerbating the frustration of the person seeking the test results.

Thus, there is a need and a desire for a method for enhancing the ability to obtain a suitable .blood specimen, whether taken at a hospital, out-patient facility, or in association with a home test kit.

SUMMARY OF THE INVENTION

In view of the above, and in accordance with one aspect of the present invention, there is provided an apparatus for enhancing blood flow from a puncture in a person. The apparatus of the present invention includes a strip of flexible or pliable material that is sized to circumferentially extend about a digit of the person from whom the blood sample is to be taken. The strip of pliable material has upper and lower generally parallel and planar surfaces. Moreover, the flexible strip or film defines a throughhole disposed between opposite ends of the strip. The bottom or lower surface of the film has a skin contacting adhesive thereon, such that when the film is tautly secured about a digit of the person, the throughhole circumscribes an underlying surface skin area that is to be punctured to create blood flow. A salient feature of the film strip is that it inhibits venous blood flow in the area of the strip, thereby enhancing blood flow from the puncture.

The film strip is preferably formed of a flexible, synthetic vinyl polymer or plastic material, having elasticity between opposite ends thereof and a thickness of about 0.005 inches between the top and bottom surfaces thereof. In a preferred form of the invention, the strip includes a central portion with oppositely directed strap portions integrally formed with and, thus, connected to and extending from the central portion. The central portion of the strip preferably defines the throughhole or aperture which preferably has a diameter greater than about 0.125 inches and that passes clearly between the top and bottom surfaces of the strip. Notably, the strip of the present invention has no pad or other material in the area of the throughhole which would absorb blood from the puncture.

In the most preferred form of the invention, the strip has a generally rectangular configuration with elongated sides disposed on opposite sides of the aperture or throughhole. The skin contacting adhesive extends across the entirety of the bottom surface. The taut application of the film strip to the person's finger or toe when configured with the adhesive securement of the strap portions to the underlying skin tends to maintain the puncture open, thus promoting blood flow from the puncture.

Another aspect of the present invention relates to a method for obtaining a blood sample from a digit, i.e., a finger or toe, of a person. Such a method comprises the steps of applying a disposable adhesive tape about a person's digit, said tape having a throughhole with a closed margin between opposite ends of said tape, and wherein said tape is tautly applied about the person's finger such that the throughhole overlies an area on the person's digit and inhibits venous blood flow in that area of the finger; and puncturing the digit in the area circumscribed by the throughhole. The method for obtaining a blood sample is enhanced by the further step of cleansing the area wherein the adhesive tape is to be applied with a disinfectant.

The apparatus and method disclosed in the present invention is equally applicable to hospitals, out-patient care facilities and in-home test kits. Regardless of where it is used, the tautly applied adhesive strip of the present invention maintains a blood sample puncture open such that more than an adequate blood specimen is provided. Upon obtaining the blood specimen, the strip of the present invention is removed from the person's digit and readily disposed of, thus allowing the person to heal in a normal manner. By restricting venus blood flow in the digit wrapped by the adhesive strip of the present invention, blood flow is enhanced even in those persons that normally present problems in obtaining adequate blood specimens. Testing has clearly indicated a significant difference in the blood flow.

Numerous other features, objects and advantages of the present invention will be readily appreciated from the following detailed description, appended claims, and the following drawings.

BRIEF DESCRIPTION OF THE DRAWINGS

FIG. 1 is a perspective view of the apparatus for enhancing bleeding according to the present invention;

FIG. 2 is a schematic top plan view of the present invention;

FIG. 3 is a schematic bottom plan view of the present invention;

FIG. 4 is a schematic side elevational view of the present invention;

FIG. 5 is a perspective view showing the application of the apparatus of the present invention to a person's finger;

FIG. 6 is a fragmentary enlarged sectional view of the present invention as shown applied to a person's finger; and FIG. 7 is a fragmentary enlarged sectional view of the present invention as shown applied to a person's finger.

DETAILED DESCRIPTION OF THE PRESENT INVENTION

While the present invention is susceptible of embodiment in various forms, there is shown in the drawings and will hereinafter be described a preferred embodiment of the invention with the understanding that the present disclosure is to be considered as setting forth an exemplification of the invention which is not intended to limit the invention to the specific embodiment illustrated.

Referring now to the drawings, wherein like reference numerals indicate like parts throughout the several views, One embodiment of an apparatus for enhancing flow in a person, according to the present invention, is schematically represented in its entirety by reference numeral 10. As shown in FIGS. 1 and 2, apparatus 10 comprises an elongated and pliable apertured strip 12. Strip 12 defines upper and lower generally parallel surfaces 14 and 16, respectively. Intermediate its opposite ends, strip 12 further defines an aperture or throughhole 18 that extends clearly through the top and bottom surfaces 14 and 16, respectively, of strip 12. It is important to note, strip 12 has no pad or other absorptive material in the area of the throughhole 18.

As shown in FIGS. 3 and 4, permanently attached to the lower or bottom surface 16 of strip 12 is a conventional medical grade adhesive 20 suitable for releasable contact with the skin of a person and preferably a hypo-allergenic synthetic pressure sensitive adhesive. The materials of the adhesive 20 are such that when the strip 10 is applied to the skin, the adhesive 20 firmly holds the strip 10 in place on the skin and/or opposite ends of strip 12 are releasably attachable in overlapping relation to each other when the strip 10 is circumferentially wrapped about a digit of a person, as described in detail below.

In the illustrated embodiment shown in FIGS. 1 and 4, and as sold, apparatus 10 includes a plastic, foil, paper, metal foil or a laminate release sheet 22 that adheres to and protects the adhesive 20. When strip 12 is to be used, sheet 22 is peeled away by the user to allow the strip or film 12 to be adhered toy the skin of a person.

Strip 12 is preferably formed from a single ply, non-absorptive material such as a flexible synthetic vinyl polymer film having a thickness of about 0.005" between the top and bottom surfaces 14 and 16, respectively. Preferably, strip 12 is stamped or otherwise removed from a web of somewhat stretchable or elasticized plastic or plastic covered, paper film that can be economically disposed of following a one time use of the apparatus 10.

In the illustrated embodiment, the aperture 18 is schematically illustrated as having a generally circular closed margin having a diameter greater than 0.125". It should be appreciated, however, that apertures having other than circular closed margins may equally suffice without detracting or departing from the spirit and scope of the present invention.

Returning to FIGS. 1 and 2, strip 12 preferably includes a central portion 26 with like strap portions 28 and 30 extending in opposite directions from the central portion 26 and which terminate in free ends 32 and 34. In a preferred form of the invention, the aperture or throughhole 18 has a closed margin defined by the central portion 26 of the strip 12 equidistant from the opposite ends 32 and 34 such that, when a stretching force is applied to the strip 10, substantially equal and oppositely directed components of stretch extend away from opposite sides of the closed margin of the aperture or throughhole 18.

As shown, strip 12 has a generally rectangular configuration including a pair of elongated sides 38 and 40 and a pair of shorter sides 42 and 44 at the terminal ends 32 and 42, respectively, of the strip 12. In the illustrated embodiment, the elongated sides 38, 40 are generally parallel to each other and are disposed on opposite sides of the aperture or throughhole 18. While the shape of strip 12 is shown as being generally rectangular in FIGS. 1 through 4, it will be appreciated that the shape of strip 12 could take other configurations without detracting or departing from the spirit and scope of the present invention.

FIGS. 5 through 7 schematically illustrate application of the strip 12 to a finger F of a person. Following removal of the peelable liner 22 to expose the adhesive 26 to the skin to which the strip 12 is to be attached, the central portion 26 of strip 12 is arranged such that the aperture 18 defined thereby overlies a pad P of the finger F. As will be appreciated from a complete understanding of the present invention, the strip 12 can be applied to any digit, i.e., finger or toe, of the person from whom a blood sample is to be taken and the application to a finger F is merely for illustrative purposes and is not to be considered limiting or restricting with respect to the spirit and scope of the present invention.

The strip 12 is circumferentially and tautly applied about the person's finger by pulling in opposite directions and with generally equal force on the strap portions 28 and 30 of the strip 12. The adhesive 20 on the bottom surface 16 allows overlapping ends of the strip 12 to be releasable attached to each other so as to maintain pressure on that area of the finger circumferentially covered by the strip 12. Alternatively, the securement of the adhesive 20 to the skin coupled with the elasticity of the strip 12 will likewise maintain pressure on that area of the digit circumferentially covered by the strip 12.

As schematically represented in FIG. 6, following the taut application of strip 12 to the finger F, the underlying skin area circumscribed by the aperture or throughhole 18 will tend to push upwardly through the aperture 18. Thus, the aperture 18 circumscribes an underlying skin surface area that is to be punctured to create blood flow. That is, the closed margin of the aperture or throughhole 18 acts as a guide to where the skin is to be punctured to create blood flow.

As schematically represented in FIG. 7, after the strip 12 is tautly applied the underlying skin surface area circumscribed by the aperture or throughhole 18 is punctured or cut C using a conventional lancet L or other suitable instrument. In a most preferred form of the invention, the adhesive 20 is applied across the entirety of the bottom surface 16 of the strip 12. Accordingly, the taut application of the film strip 12 to the person's finger coupled with the adhesive securement of the strap portions 28 and 30 to the underlying skin tends to pull in the directions of the arrows thereby maintaining the puncture or cut C open thus enhancing blood flow therefrom. Moreover, the taut application of the strip 12 to the person's digit has a tourniquet effect thus restricting venus blood flow and thereby promoting or enhancing blood flow from the puncture C.

Prior to applying the strip 12 to the person's finger or toe, the area that is to be punctured is preferably cleansed using a suitable cleansing agent, i.e., alcohol.

From the foregoing it will be apparent that the present invention functions effectively to significantly enhance blood flow from punctures even in those person's who tend to have difficulty bleeding. The taut application of the strip 12 serves to restrict venus blood flow and, thus, promote bleeding from the puncture created. Moreover, the kinetic tension in the adhesively secured strap portions 28 and 30 of strip 12 maintains the cut or puncture C open thereby enhancing blood flow to promote collection of a suitable blood test specimen. Because of the economic materials from which the present invention is fabricated, after a suitable blood test specimen has been obtained, the strip 12 is removed and suitably discarded, Moreover, it should be apparent that the present invention is equally applicable in hospitals, out-patient facilities, in-home test kits and wherever else blood test specimens are to be obtained.

From the foregoing, it will be observed that numerous modifications and variations can be effected without departing from the true spirit and scope of the novel concept of the present invention. It will be appreciated that the present disclosure is intended as an exemplification of the invention, and is not intended to limit the invention to the specific embodiment illustrated. The disclosure is intended to cover by the appended claims all such modifications as fall within the scope of the claims.

What is claimed is:

1. A method for obtaining a blood sample from a person's finger comprising the steps of:

applying a disposable adhesive non-absorptive tape about a person's finger, said tape having a throughhole with a an inner peripheral surface defined by and between opposite ends of said tape, with the peripheral surface of said throughhole defining an unobstructed passage extending through said tape, and wherein said tape is tautly applied about the person's finger such that the throughhole overlies a finger pad on the person's finger and inhibits venus blood flow in that area of the finger; and puncturing the finger pad of the person in the area circumscribed by the throughhole.

2. The method according to claim 1 further comprising the step of cleansing the finger area wherein the adhesive tape is to be applied with a disinfectant.

* * * * *